(12) United States Patent
Naya

(10) Patent No.: US 6,947,145 B2
(45) Date of Patent: Sep. 20, 2005

(54) MEASURING APPARATUS

(75) Inventor: Masayuki Naya, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 250 days.

(21) Appl. No.: 10/630,713

(22) Filed: Jul. 31, 2003

(65) Prior Publication Data

US 2004/0109162 A1 Jun. 10, 2004

(30) Foreign Application Priority Data

Jul. 31, 2002 (JP) ........................................ 2002-223231

(51) Int. Cl.[7] ............................................. G01N 21/17
(52) U.S. Cl. ....................................................... 356/445
(58) Field of Search ................................. 356/445–448

(56) References Cited

U.S. PATENT DOCUMENTS 5,485,277 A * 1/1996 Foster ......................... 356/445
2002/0140938 A1 * 10/2002 Naya et al. .................. 356/445
2003/0075697 A1 * 4/2003 Ohtsuka et al. ............. 250/573
2003/0156292 A1 * 8/2003 Naya .......................... 356/445

FOREIGN PATENT DOCUMENTS

JP 6-167443 A 6/1994
JP 2003-227792 * 8/2003

* cited by examiner

Primary Examiner—Michael P. Stafira
(74) Attorney, Agent, or Firm—Sughrue Mion, PLLC

(57) ABSTRACT

A measuring apparatus for measuring the state of attenuated total reflection over time for a single measuring unit without being affected by the change in measuring conditions arising from replacement and resetting of the sample. A light beam is entered into the interface between a dielectric block and a metal film having a dielectric film thereon at various incident angles within the angle range that creates two or more dark lines due to attenuated total reflections, and the variation in the positions of other dark lines are measured with reference to the dark line having the least positional variation among them.

16 Claims, 3 Drawing Sheets

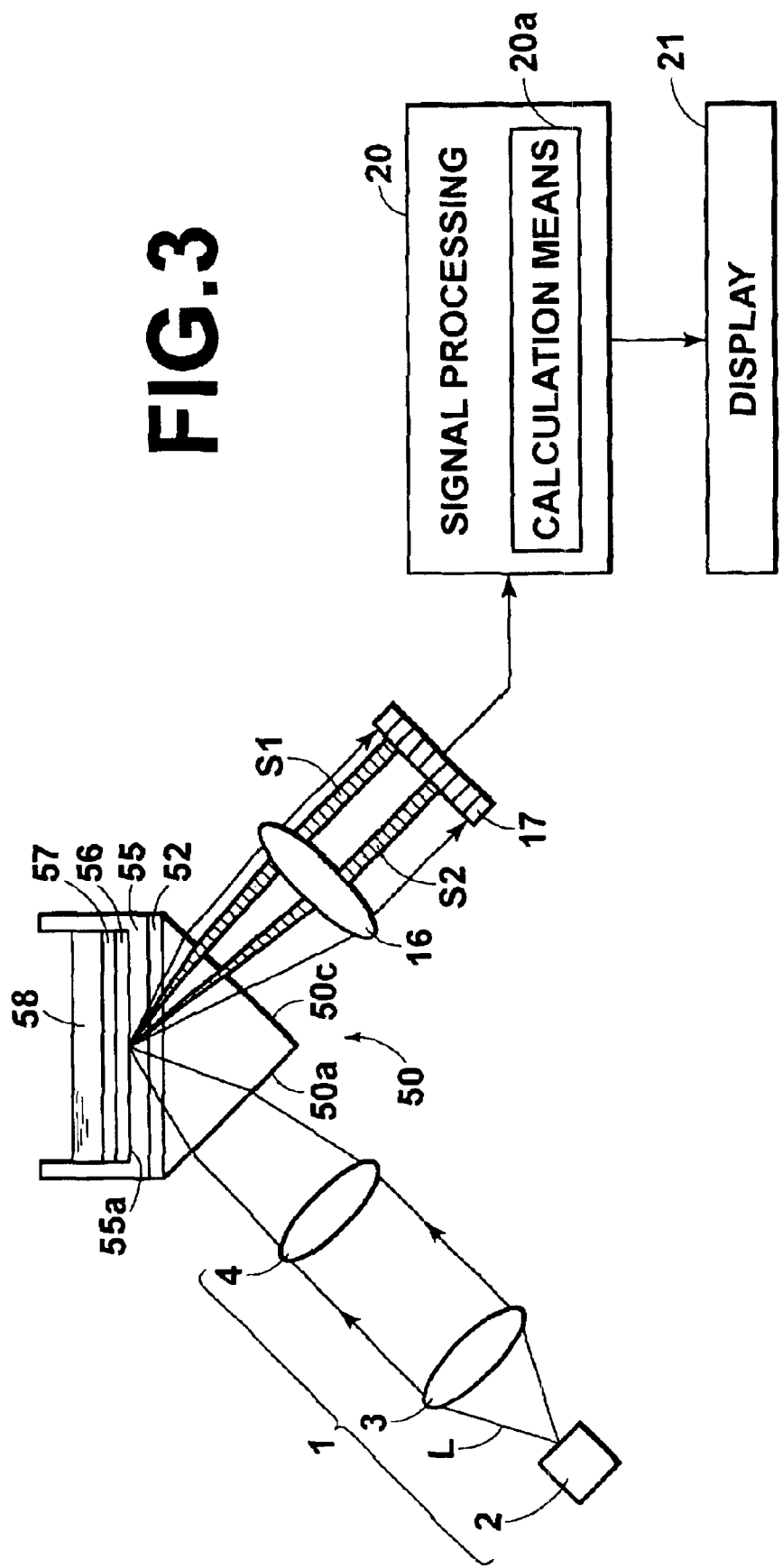

MEASURING APPARATUS

BACKGROUND OF THE INVENTION

1. Field of the Invention

The present invention relates to a measuring apparatus for sample analysis using an evanescent wave generated when a light beam is totally reflected.

2. Description of the Related Art

In a metal, free electrons oscillate as a group and a compressional wave called a plasma wave is generated. The quantized compressional waves generated on the surface of a metal are known as surface plasmons.

Various surface plasomon sensors have been proposed for quantitative analysis of a substance in a sample by applying the phenomenon that the surface plasmons are excited by a light wave. Among these sensors, the one that uses a system called Kretschmann geometry is particularly well-known as described, for example, in Japanese Unexamined Patent Publication No.6 (1994)-167443.

Basically, the surface plasmon sensor that uses the system described above comprises, for example, a dielectric block shaped like a prism; a metal film formed on one of the surfaces of the dielectric block and brought into contact with a sample; a light source for generating a light beam; an optical system for entering the light beam into the dielectric block at various angles to satisfy the conditions of total reflection at the interface between the dielectric block and the metal film, and to cause attenuated total reflection by surface plasmon resonance; and a light detecting means for detecting the state of surface plasmon resonance or attenuated total reflection by measuring the intensity of the light beam totally reflected at the interface.

In order to obtain a light beam having the various incident angles described above, a comparatively narrow light beam may be entered into the interface by changing its incident angle, or a comparatively wide light beam may be entered thereto as a converging or diverging light beam to include light components that are incident on the interface at various angles. In the first case, the reflected light beam that changes its reflection angle in accordance with its incident angle may be detected by a small light detector that moves in synchronization with the change in the reflection angle, or by an area sensor that extends along the changing direction of the reflection angle. In the latter case, the reflected light beam may be detected by an area sensor that extends along the direction where all of the light components of the light beam reflected at various angles may be captured.

When a light beam enters the metal film of a surface plasom sensor configured in the aforementioned manner at a certain incident angle $\theta_{sp}$ which is greater than the total reflection angle, an evanescent wave having a distributed electric field in the sample in contact with the metal film is generated, and thereby surface plasoms are excited at the interface between the metal film and the sample. When the wave-number matching is achieved, in which the wave-number vector of the evanescent light matches the wave-number vector of the surface plasmons, the evanescent light and the surface plasmons go into the sate of resonance, and the intensity of the light totally reflected at the interface between the dielectric block and the metal film drops sharply, because the light energy is transferred to the surface plasmons. This drop in the intensity of light is generally detected as a dark line by the light detecting means described above.

The resonance described above occurs only when a p-polarized light beam enters the metal film. Accordingly, arrangements need to be made in advance so that the light beam enters the metal film in p-polarized mode, or only p-polarized light components are detected by the light detecting means.

When the wave-number of the surface plasmons is determined from the incident angle $\theta_{sp}$ that causes attenuated total reflection (ATR), the dielectric constant of the sample may be obtained. More specifically, the following relationship may be derived, assuming that Ksp as the wave-number of surface plasmons, $\omega$ as the angular frequency of the surface plasmons, c as speed of light in vacuum, $\epsilon_m$ as the dielectric constant of the metal, and $\epsilon_s$ as the dielectric constant of the sample.

$$K_{SP}(\omega) = \frac{\omega}{c} \sqrt{\frac{\varepsilon_m(\omega)\varepsilon_s}{\varepsilon_m(\omega) + \varepsilon_s}}$$

When the dielectric constant $\epsilon_s$ is determined, the density of a particular substance in the sample may be obtained based on a predefined calibration curve, and the like. That is, by determining $\theta_{sp}$ that causes the drop in the reflected intensity of light described above, the dielectric constant of the sample or characteristics related to the refractive index of the sample may be obtained.

The leakage mode sensor described, for example, on pages 21 to 23, and 26 to 27 of "BUNKOH KENKYU", Vol. 47, No.1 (1998) is also known as a similar sensor that uses attenuated total reflection (ATR). Basically, the leakage mode sensor comprises, for example, a dielectric block shaped like a prism; a cladding layer formed on one of the surfaces of the dielectric block; an optical guiding layer formed on the cladding layer and brought into contact with the sample; a light source for generating a light beam; an optical system for entering the light beam into the dielectric block at various angles to satisfy the conditions of total reflection at the interface between the dielectric block and the cladding layer, and to cause attenuated total reflection by the excitation of guided mode in the optical guiding layer; and a light detecting means for detecting the state of excitation of guided mode or attenuated total reflection by measuring the intensity of the light beam totally reflected at the interface.

When a light beam is incident on the cladding layer through the dielectric block of a leakage mode sensor configured in the aforementioned manner at a certain incident angle which is equal to or greater than the total reflection angle, certain light components of the light beam having particular wave-numbers and incident angles pass through the cladding layer, and propagate along the optical guiding layer in guided mode. When the guided mode is excited in this manner, attenuated total reflection occurs, in which the intensity of the light totally reflected at the interface described above drops sharply, because most of the light components of the light beam are contained in the optical guiding layer. The wave-number of the guided light is dependent on the refractive index of the sample placed on the optical guiding layer, so that the refractive index of the sample and other characteristics related thereto may be analyzed by determining the particular incident angle that causes the attenuated total reflection described above.

Various types of measuring apparatuses are available that utilize attenuated total reflection of a surface plasmon sensor, leakage mode sensor, or the like, such as an apparatus that enters a light beam containing a plurality of light components of different wavelength into the interface, and detects the level of attenuated total reflection for each wavelength, or an apparatus that splits up a portion of the light beam to be entered into the interface before entering and mixes up the split-up light beam with the light beam reflected at the interface to interfere with each other, and measures the state of the interference, as well as an apparatus that measures a particular incident angle that causes attenuated total reflection described above, in the process of analyzing characteristics of a subject under test by entering light to the interface with an angle that satisfies the conditions of total reflection, and measuring changes in the state of the light totally reflected at the interface due to the evanescent wave generated by the light entered into the interface.

In the conventional surface plasmon sensor, or leakage mode sensor described above, a sample is sometimes replaced together with the dielectric block in order to efficiently conduct measurement for a plurality of samples, when the sample (same measuring unit) needs to be measured a plurality of times at intervals to analyze changes in the state of the sample over time. In this case, when the sample is reset on the measuring apparatus for measurement after replacement, a difference (in inclination) may arise between the initial baseline (interface described above) and the latter baseline. If this difference in inclination between the two baselines is a difference in the vertical inclination that changes the incident angle of the light beam entering at various incident angles, then the reflection angle of the reflected light beam is also deviated, thereby the accuracy of the measurement is lost.

Even when a sample replacement does not take place, changes in the inclination of the baseline may occur subtly by vibrations, or the like, when a plurality of measuring units is moved or rotated on a support or rotating platform. In such a case, changes in the inclination of the baseline developed during a plurality of measurements cause measurement errors.

SUMMARY OF THE INVENTION

The present invention has been developed in recognition of the circumstance described above and it is an object of the present invention to provide a high-accurate measuring apparatus by preventing measurement errors caused by changes in the inclination of the interface where a light beam is totally reflected, in conducting measurement a plurality of times for a single measuring unit.

The measuring apparatus according to the present invention comprises:

a measuring unit having a transparent dielectric block, a metal film formed on one of the surfaces of said dielectric block, and a transparent dielectric film formed on said metal film;

a light beam entering means for entering a light beam into said dielectric block at various incident angles within an angle range that satisfies the conditions of total reflection at the interface between said dielectric block and said metal film, and creates two or more dark lines due to attenuated total reflections in a light beam totally reflected at said interface;

a light detecting means for receiving said light beam totally reflected at said interface, and detecting positions on a light receiving surface of said two or more dark lines contained therein; and a calculation means for calculating a variation in each of said positions of said two or more dark lines on said light receiving surface arising from a change in the dielectric constant of a substance placed on said transparent dielectric film with reference to one of said two or more dark lines having the least positional variation on the light receiving surface among said two or more dark lines, based on the output of said light detecting means.

At least one of the "two or more dark lines" is a dark line created by the attenuated total reflection due to surface plasmon resonance occurred on the interface between the dielectric block and the metal film, and others are those created by the attenuated total reflection due to excitation of light-guided mode.

More specifically, the measuring apparatus according to the present invention causes attenuated total reflections by the excitation of surface plasmons and light-guided mode simultaneously, which are respectively the feature of the surface plasmon sensor and the leakage mode sensor as described above, and detects the dark lines created by these attenuated total reflections. The applicant has found that providing a transparent dielectric film on the metal film of the measuring unit causes the change in the dielectric constant of a substance (sample) placed thereon to have an impact only on the wave-number that induces light-guided mode, and substantially not on the wave-number that induces surface plasmons, creating a stable dark line that remains at substantially the same position on the light receiving surface. The measuring apparatus according to the present invention opened a way for accurate measurement by preventing measurement errors caused by, for example, changes in the inclination of the interface, and the like by incorporating the finding described above and by measuring a variation in each of the positions of the dark lines on the light receiving surface using the aforementioned stable dark line as the reference. In addition, the measuring apparatus according to the present invention enters a light beam into the interface in p-polarized mode with respect to the interface in order to achieve surface plasmon resonance.

Further, "the position on the light receiving surface" described above corresponds to the incident angle of the light beam at the interface (the reflection angle at the interface), and detecting the position of the dark line on the light receiving surface is equivalent to detecting the incident angle of the light beam at the interface.

As for the reference dark line described above, a dark line created by a light component having the largest incident angle at the interface may be used among the two or more dark lines described above.

A sensing material may be fixed on the dielectric film of the measuring unit described above, and the change in the dielectric constant described above may be the change in the dielectric constant arising from a reaction when a test substance containing a material that reacts to the sensing material is brought into contact with the sensing material. That is, in this case, both the sensing material and material that reacts to the sensing material are the intended samples for the measurement.

Preferably, the thickness of the metal film is 10 nm to 70 nm, and the thickness of the transparent dielectric film is 100 nm and 2000 nm Preferably, the transparent dielectric film is made of $SiO_2$, a glass, or plastic material.

Further, the dielectric block described above may be a dielectric block formed as a single block having the entrance and outgoing surfaces for the light beam, and a surface the metal film is formed thereon, or it may comprise a component having the entrance and outgoing surfaces for the light beam, and a component having a surface the metal film is formed thereon, connected to each other through a refractive index matching means.

As for the light detecting means for the measuring apparatuses described above, a photodiode array, CCD, or the like may be preferably used.

The measuring apparatus according to the present invention comprises a measuring unit having a transparent dielectric block, a metal film formed on one of the surfaces of the dielectric block, and a transparent dielectric film formed on the metal film, so that it may create two or more dark lines due to attenuated total reflections when a light beam is entered into the interface between the dielectric block and the metal film at various incident angles through the dielectric block.

Further, the measuring apparatus according to the present invention further comprises a light beam entering means for entering a light beam into the interface at various incident angles within the angle range that creates two or more dark lines, and a light detecting means for detecting the positions on the light receiving surface of the two or more dark lines contained in the light beam totally reflected at the interface, and a calculation means for calculating a variation in each of the positions of the two or more dark lines on the light receiving surface arising from a change in the dielectric constant of a substance placed on the transparent dielectric film with reference to the dark line having the least positional variation on the light receiving surface among the two or more dark lines, based on the output of the light detecting means, so that the measuring apparatus may obtain a measurement result that cancels out errors arising from the change in the inclination of the interface that vary the incident angle of the light beam at the interface, and the like.

When the measuring apparatus according to the present invention further comprises a sensing material fixed on the dielectric film of the measuring unit described above, and adapted to detect the change in the dielectric constant when a test substance containing a material that reacts to the sensing material is brought into contact with the sensing material, it maybe used for the measurement of antigen-antibody reactions, and the like.

Selection of the thickness of the metal film and the transparent dielectric film in the ranges from 10 nm to 70 nm, and from 100 nm to 2000 nm respectively may create two dark lines due to attenuated total reflections, in which case a signal of higher signal-to-noise ratio may be obtained compared with the case in which three or more dark lines are created.

BRIEF DESCRIPTION OF THE DRAWINGS

FIG. 3 is a side view of a measuring apparatus according to a second embodiment of the present invention.

DESCRIPTION OF THE PREFERRED EMBODIMENTS

Hereinafter, the preferred embodiments of the present invention will be described in detail with reference to the accompanying drawings.

Figure 1:
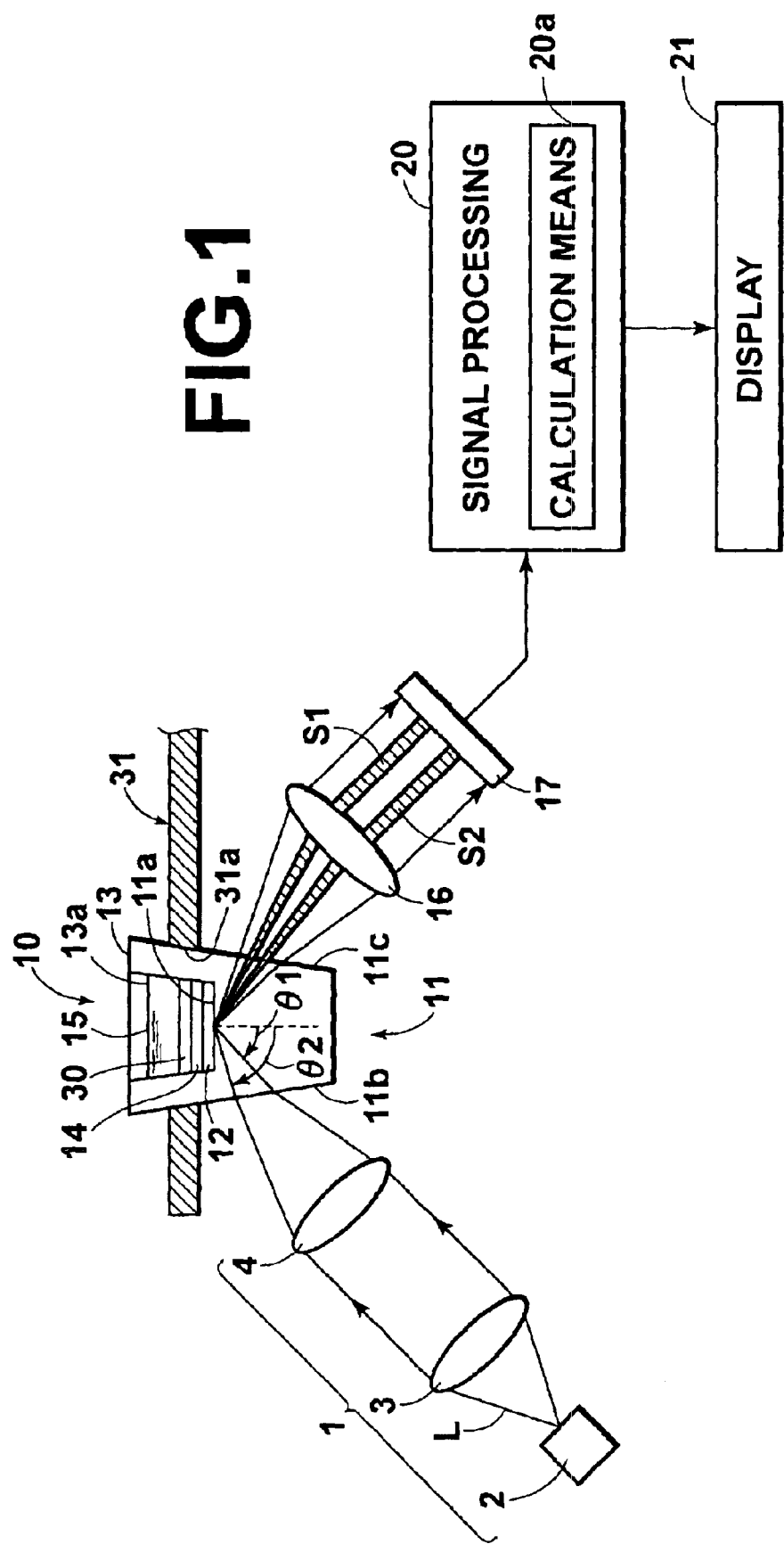
FIG. 1 is a side view of a measuring apparatus according to a first embodiment of the present invention.

FIG. 1 is a side view of a measuring apparatus according to a first embodiment of the present invention.

As shown in the FIG. 1, the measuring apparatus according to the first embodiment has a measuring chip 10 as a measuring unit. The measuring chip 10 has a test substance holding section 13 made of, for example, transparent resin, or the like shaped like a frustum of an inverted quadrangular pyramid, and has a circular-section test substance holding hole 13a on the upper side. The test substance holding hole 13a is clad with a metal film 12 made of Au on the bottom (a surface 11a of a dielectric block 11, which will be described later), and a transparent dielectric film 14 made of $SiO_2$ formed thereon, and a sample solution 15 is held on the transparent dielectric film 14. The lower part of the test substance holding section 13 of the measuring unit 10 is a dielectric block 11, and two surfaces facing to each other of the four side surfaces of the dielectric block are used as a light entrance surface 11b and a light outgoing surface 11c respectively. That is, the dielectric block 11 is formed as a single block having the light entrance surface 11b, the light outgoing surface 11c, and a surface the thin film layer (metal film) 12 is formed thereon. The dielectric block according to the first embodiment has a sensing material 30 fixed on the dielectric film 14, which will be described later.

The thickness of the metal film is 10 nm to 70 nm, and the thickness of the transparent dielectric film is 100 nm to 2000 nm.

Each of the measuring chips 10 is fitted firmly into each of a plurality of unit holding holes 31a created, for example, through a turntable 31. The turntable 31 rotates intermittently by a certain predefined angle at a time after the measuring chips 10 are attached thereto in this manner, and the sample solution 15 is dropped and held in the test substance holding section 13 of the measuring chip 10 that stopped at a prescribed position. Thereafter, the turntable 31 further rotates by a certain predefined angle to move the measuring chip 10 to a position shown in FIG. 1, and stops there.

In addition to the measuring chip 10, which is the measuring unit described above, the measuring apparatus according to the first embodiment further comprises a light beam entering means for entering a light beam L from the entrance surface 11b of the dielectric block 11 to an interface 11a between the dielectric block 11 and the metal film 12 at various incident angles; a collimator lens 16 for collimating the light beam L totally reflected at the interface 11a; a light beam detecting means 17 for detecting the collimated light beam L; a signal processing section 20 having a calculation means 20a; and a display section 21 connected to the signal processing section 20.

The light beam entering means 1 comprises a light source 2 made of a semiconductor laser, or the like for generating the light beam L, a collimator lens 3 for collimating the light beam L emitted from the light source 2 in diverging mode, and a converging lens 4 that converges the collimated light beam L at the interface 11a.

As shown in FIG. 1, the light beam L emitted from the light source 2 in diverging mode is converged at the interface 11a between the dielectric block 11 and the metal film 12 by the operation of lenses 3 and 4. Accordingly, the light beam L contains light components having various incident angles (from θ1 to θ2) at the interface 11a, which are equal to or greater than the total reflection angle. The light beam L is totally reflected at the interface 11a, and the reflected light beam L, therefore, contains light components having various reflection angles. The light beam L is entered into the interface 11a in p-polarized mode with respect to the interface 11a. In order to obtain a p-polarized light beam L with respect to the interface 11a, the light source 2 may be prearranged so that the direction of the polarization becomes the prescribed direction. A wavelength plate or polarization plate may be used as an alternative means for controlling the direction of the polarization of the light beam L. Further, the light beam entering means 1 may be configured to enter the light beam L into the interface 11a in defocused mode. By doing so, measurement errors in the measurement of the positions of the dark lines described above are averaged, and hence the accuracy of the measurement is enhanced.

The light beam L totally reflected at the interface 11a and collimated by the collimator lens 16 is detected by the light detecting means 17. The light detecting means 17 of the measuring apparatus according to the first embodiment is a CCD line sensor, which is disposed so that its longitudinal direction becomes substantially perpendicular to the traveling direction of the collimated light beam L in the plane of FIG. 1. Accordingly, the light components of the light beam L totally reflected at the interface 11a at various angles are received at the respective longitudinal positions of the line sensor. That is, the position of each of the light components of the light beam L on the light receiving surface of the line sensor corresponds uniquely to the reflection angle of each of light components at the interface 11a (i.e., incident angle at the interface). As for the light detecting means 17, a photodiode array made of a plurality of photodiodes arranged in the longitudinal direction of the line sensor may be used, as well as a CCD line sensor.

Figure 2:
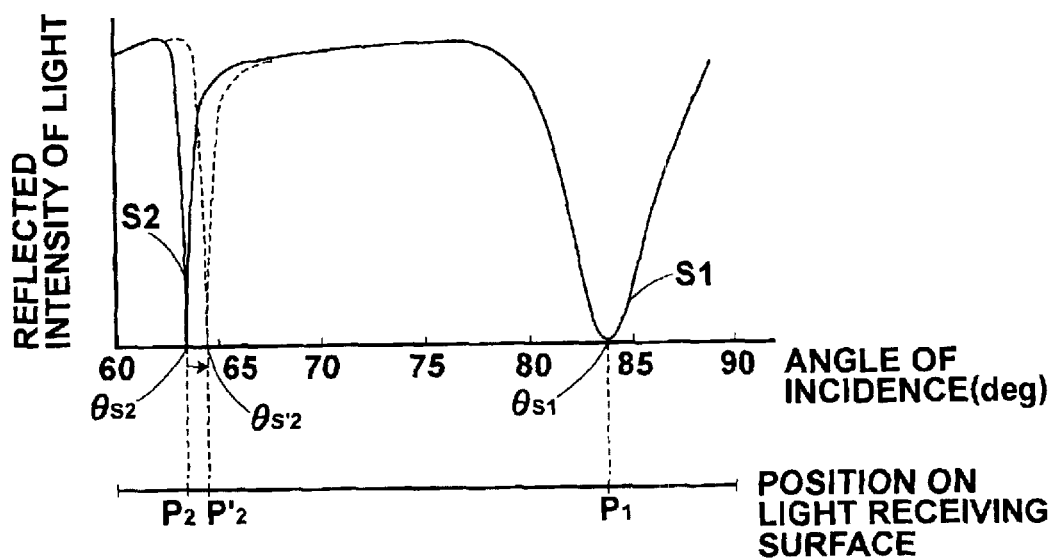
FIG. 2 is a drawing illustrating a relationship between the incident angle of the light beam entered and the reflected intensity of the light beam detected by the measuring apparatus shown in the FIG. 1.

FIG. 2 shows the relationship between the incident angle θ of the light beam L totally reflected at the interface 11a and the position on the light receiving surface of the light detector with its intensity I.

As shown in FIG. 2, when a light beam L is entered into the measuring chip 10 of the measuring apparatus according to the first embodiment, that is, a measuring chip 10 comprising a metal film 12, and a transparent dielectric film 14 formed thereon, at incident angles that satisfy the conditions of total reflection at the interface 11a between the dielectric block 11 and the metal film 12, a plurality of dark lines, S1 and S2, is created due to attenuated total reflections at a plurality of incident angles within the angle range that satisfies the conditions of total reflection. One of the dark lines remains substantially unaffected by the change in the dielectric constant of a sample placed on the transparent dielectric film, while the other dark line moves widely by the change in the dielectric constant of the sample.

The light component entered the interface 11a at a particular incident angle $\theta_{S1}$ excites surface plasmons at the interface between the metal film 12 and the transparent dielectric film 14, so that the reflected intensity I of the light component drops sharply (dark line S1 in FIG. 2). In addition, the light component entered the interface 11a at another particular incident angle $\theta_{S2}$ excites light-guided mode in the transparent dielectric film 14, so that the reflected intensity I of the light component also drops sharply (dark line S2 in FIG. 2). The wave-number of guided light in the transparent dielectric film 14 is heavily dependent on the dielectric constant of the sample placed on the dielectric film 14, and if the dielectric constant changes, the incident angle that creates dark line S2 due to attenuated total reflection caused by the excitation of light-guided mode changes, for example, as shown in the dotted line in FIG. 2. That is, the dark line S2 appeared at the incident angle $\theta_{S2}$ now appears, for example, at the incident angle $\theta_{S2}'$. On the other hand, the dark line S1 due to attenuated total reflection caused by the excitation of surface plasmons is dependent on the dielectric constant of the dielectric film 14 on the metal film 12, which is not affected by the change in the dielectric constant of the sample, so that the incident angle $\theta_{S1}$, that creates the dark line S1 remains substantially unchanged.

FIG. 2 shows the case in which two dark lines are created, but the light-guided mode may couple to a plurality of light components having different incident angles. In that case, a plurality of dark lines that move widely is created by the change in the dielectric constant of the sample placed on the transparent dielectric film 14. However, a signal of highest signal-to-noise ratio may be obtained under the condition in which two dark lines are created as shown in FIG. 2. Two dark lines, one by the excitation of surface plasmons, and the other by the excitation of light-guided mode, may be obtained by selecting an appropriate thickness for the metal film and the dielectric film within the respective ranges described above.

The measuring apparatus according to the present invention makes use of the fact that the position of the dark line S1 (an incident angle creating the dark line S1) on the light receiving surface created by the attenuated total reflection due to excitation of surface plasmons remains substantially unaffected by the change in the dielectric constant of the sample, and measures the change in the dielectric constant of a sample by obtaining a variation in the position of the dark line S2 created by the attenuated total reflection due to excitation of light-guided mode with reference to the dark line S1.

As described above, the incident angle of the light beam L at the interface corresponds uniquely to the position on the light receiving surface of the light detector, so that the change in the incident angles creating the dark lines S1 and S2 may be obtained by detecting the variation in the positions P1 and P2 of the dark lines S1 and S2 on the light receiving surface. That is, the change in the incident angles creating the dark lines S1 and S2 indicates the change in the dielectric constant (refractive index) of a sample, so that the change in the dielectric constant of a sample over time may be obtained by detecting the variation in the positions of the dark lines S1 and S2 over time on the light receiving surface of the light detector.

The calculation means 20a calculates the distance ΔP between a position P1 of the dark line S1 and a position P2 of the dark line S2 at each measuring time (ΔP=P2(t)−P1(t)). The signal processing section 20 obtains the change in the dielectric constant (refractive index) of the sample based on the variation in the ΔP over time, and the measurement result is displayed on the display 21.

The measuring apparatus according to the first embodiment has a sensing material fixed on the transparent dielectric film 14, which combines with a particular substance contained in a sample solution, and the dielectric constant of the sensing material 30 changes in accordance with the combined state, so that the change in the combined state may be studied by continuously measuring the distance between the two dark lines S1 and S2. That is, both the sample solution and the sensing material 30 are the intended samples for analysis. A combination of such particular substance and the sensing material 30 includes, for example, a combination of an antigen and antibody.

In addition to calculating the distance ΔP(t) between the two dark lines at predefined time intervals, the difference between the initial difference ΔP(0) and the difference ΔP(t) measured after a predetermined time from the initial measurement (ΔP(t)−ΔP(0)) may be calculated in order to study the change in the combined state of a particular substance and the sensing material 30 over time.

In measuring the change in the combined state of the sensing material and a particular substance over time as described above, a single measuring chip is measured a plurality of times at predefined time intervals. When such measurement is conducted, the measuring chip 10 is removed from the turntable 31 after it is measured, and the next measuring chip that holds another sample is mounted on the turntable 31 and measured, then the initial chip 10 is reset thereon for the next measurement after a predetermined time.

In resetting the measuring chip 10, a difference in the measuring conditions from the previous measurement may occur. That is, the change in the vertical inclination of the interface 11a that changes the incident angle of the light beam L at the interface 11a may occur, causing a deviation in the positions of the dark lines. As described above, the measuring apparatus according to the first embodiment, however, always detects two or more dark lines and calculates the variation in the positions of the dark lines with reference to the dark line S1 which is not affected by the change in the dielectric constant of a sample, so that it may obtain a measurement result that cancels out the influence of the change, if any, in the inclination of the interface.

As for the cause of the change in the inclination of the interface at each measurement for a plurality of measurements for a single measuring chip includes but not limited to the vibration of the support when it is rotated or moved, and relocation of the support, light source, light detector, and the like, as well as resetting of the measuring chip described above.

Further, in measuring the state of attenuated total reflection of a sample, in which the state of attenuated total reflection of the measuring chip 10 itself or the measuring chip 10 that holds only a solvent for the sample is measured before dispensing the sample solution 15, and the bulk effect of the measuring chip 10 (and solvent) is subtracted from the measurement result obtained after dispensing the sample solution, if a change in the inclination of the interface is developed before and after the dispensing of the sample solution, the reliability of the measurement result is lost.

The measuring apparatus according to the first embodiment of the present invention always detects two or more dark lines and calculates the variation in the positions of the dark lines with reference to the dark line S1 which is not affected by the change in the dielectric constant of a sample, so that it may obtain a highly accurate measurement result that suppresses the impact of the aforementioned changes in the interface.

A measuring apparatus according to a second embodiment of the present invention will be described with reference to FIG. 3.

The measuring apparatus according to the second embodiment is a surface plasmon sensor that utilize surface plasmon resonance as in the first embodiment, and FIG. 3 is a side view thereof. Elements identical to those of the apparatus shown in FIG. 1 are given the same numerical symbols and will not be elaborated further here.

The measuring apparatus according to the second embodiment of the present invention uses a measuring unit which is different in structure from that used in the measuring apparatus shown in FIG. 1. More specifically, the measuring apparatus of the second embodiment uses a measuring unit having a triangular prism 50 made of a dielectric material, which extends to the direction perpendicular to the surface of FIG. 3, and a dielectric plate 55 connected to the upper surface of the prism 50 through refractive index matching oil 52, instead of using the measuring chip 10 used for the measuring apparatus shown in FIG. 1. The prism 50 has an entrance surface 50a and an outgoing surface 50b for a light beam L, while the dielectric plate 55 has a metal film 56 and a transparent dielectric film 57 formed thereon in this order. The light beam L enters from the entrance surface 50a, and is totally reflected at the interface 55a between the dielectric plate 55 and the metal film 56, and emerges from the outgoing surface 50b. That is, the measuring unit of the second embodiment uses a dielectric block that comprises a section 50 having the entrance surface 50a and the outgoing surface 50b for the light beam L, and a section 55 having the surface the metal film is formed thereon, each formed as a separate body, and used as a measuring unit by connecting them through the refractive index matching means (refractive index matching oil) 52. Accordingly, a sample 58 placed on the transparent dielectric plate 55 is removable together with the dielectric plate 55 from the prism 50.

The measuring apparatus of the second embodiment enters the light beam into the interface 55a between the dielectric plate 55 and the metal film 56 by the light beam entering means 1 at various incident angles within the angle range that satisfies the conditions of total reflection at the interface and creates two dark lines, detects the positions of the two dark lines by the light detecting means 17, and measures the distance (difference) between the two dark lines to obtain the change in the dielectric constant of the sample 58 placed on the transparent dielectric film 57, as in the case of the measuring apparatus of the first embodiment. Accordingly, the measuring apparatus according to the second embodiment may obtain a measurement result that is not affected by the change in the inclination of the interface 55a arising from, for example, resetting the dielectric block on the prism 50 through the matching oil 52 after a certain period of time from the time when it was removed in order to efficiently carry out the measurement for a plurality of samples.

In addition, if a sensing material is disposed on the transparent film 57, as in the measuring apparatus of the first embodiment, the measuring apparatus of the second embodiment may perform measurement of the combined state of the sensing material and a particular substance contained in the sample solution injected thereon.

What is claimed is:

1. A measuring apparatus comprising:
   a measuring unit having a transparent dielectric block, a metal film formed on one of the surfaces of said dielectric block, and a transparent dielectric film formed on said metal film;
   a light beam entering means for entering a light beam into said dielectric block at various incident angles within an angle range that satisfies the conditions of total reflection at the interface between said dielectric block and said metal film, and creates two or more dark lines due to attenuated total reflections in a light beam totally reflected at said interface;
   a light detecting means for receiving said light beam totally reflected at said interface, and detecting positions on a light receiving surface of said two or more dark lines contained therein; and
   a calculation means for calculating a variation in each of said positions of said two or more dark lines on said light receiving surface arising from a change in the dielectric constant of a substance placed on said transparent dielectric film with reference to one of said two or more dark lines having the least positional variation on said light receiving surface among said two or more dark lines, based on the output of said light detecting means.

2. A measuring apparatus according to claim 1, wherein said dark line having the least positional variation is a dark line created by a light component of said light beam having the largest incident angle at said interface among said two or more dark lines.

3. A measuring apparatus according to claim 1, wherein said measuring unit further comprises a sensing material fixed on said dielectric film, and said change in the dielectric constant is a change in said dielectric constant arising from a reaction when a test substance containing a material that reacts to said sensing material is brought into contact with said sensing material.

4. A measuring apparatus according to claim 2, wherein said measuring unit further comprises a sensing material fixed on said dielectric film, and said change in the dielectric constant is a change in said dielectric constant arising from a reaction when a test substance containing a material that reacts to said sensing material is brought into contact with said sensing material.

5. A measuring apparatus according to claim 1, wherein said metal film has a thickness of 10 nm to 70 nm, and said transparent dielectric film has a thickness of 100 nm to 2000 nm.

6. A measuring apparatus according to claim 2, wherein said metal film has a thickness of 10 nm to 70 nm, and said transparent dielectric film has a thickness of 100 nm to 2000 nm.

7. A measuring apparatus according to claim 3, wherein said metal film has a thickness of 10 nm to 70 nm, and said transparent dielectric film has a thickness of 100 nm to 2000 nm.

8. A measuring apparatus according to claim 4, wherein said metal film has a thickness of 10 nm to 70 nm, and said transparent dielectric film has a thickness of 100 nm to 2000 nm.

9. A measuring apparatus according to claim 1, wherein said transparent dielectric film is made of $SiO_2$, a glass, or plastic material.

10. A measuring apparatus according to claim 2, wherein said transparent dielectric film is made of $SiO_2$, a glass, or plastic material.

11. A measuring apparatus according to claim 3, wherein said transparent dielectric film is made of $SiO_2$, a glass, or plastic material.

12. A measuring apparatus according to claim 4, wherein said transparent dielectric film is made of $SiO_2$, a glass, or plastic material.

13. A measuring apparatus according to claim 5, wherein said transparent dielectric film is made of $SiO_2$, a glass, or plastic material.

14. A measuring apparatus according to claim 6, wherein said transparent dielectric film is made of $SiO_2$, a glass, or plastic material.

15. A measuring apparatus according to claim 7, wherein said transparent dielectric film is made of $SiO_2$, a glass, or plastic material.

16. A measuring apparatus according to claim 8, wherein said transparent dielectric film is made of $SiO_2$, a glass, or plastic material.

* * * * *